(12) United States Patent
Kagawa

(10) Patent No.: US 8,289,386 B2
(45) Date of Patent: Oct. 16, 2012

(54) SHEET-LIKE PRODUCT INSPECTING METHOD AND DEVICE

(75) Inventor: Yoshikiyo Kagawa, Takamatsu (JP)

(73) Assignee: Purex Corporation, Takamatsu-shi (JP)

( * ) Notice: Subject to any disclaimer, the term of this patent is extended or adjusted under 35 U.S.C. 154(b) by 531 days.

(21) Appl. No.: 12/594,487

(22) PCT Filed: Apr. 4, 2007

(86) PCT No.: PCT/JP2007/057530
§ 371 (c)(1),
(2), (4) Date: Dec. 17, 2009

(87) PCT Pub. No.: WO2008/120400
PCT Pub. Date: Oct. 9, 2008

(65) Prior Publication Data
US 2010/0110173 A1    May 6, 2010

(30) Foreign Application Priority Data

Apr. 2, 2007   (JP) .................................. 2007-96498

(51) Int. Cl.
*H04N 7/18* (2006.01)
*G06F 15/16* (2006.01)
(52) U.S. Cl. .......................................................... 348/88
(58) Field of Classification Search ...................... 348/88
See application file for complete search history.

(56) References Cited

U.S. PATENT DOCUMENTS

| 5,087,822 | A  | * | 2/1992 | Fairlie et al. | ............. | 250/559.46 |
| 5,691,811 | A  | * | 11/1997 | Kihira | ........................ | 356/239.1 |
| 6,668,144 | B2 | * | 12/2003 | Maruyama | ..................... | 399/45 |
| 8,144,313 | B2 | * | 3/2012 | Numata et al. | .................. | 356/71 |
| 2001/0021042 | A1 | * | 9/2001 | Hirota et al. | .................. | 358/505 |
| 2005/0229941 | A1 | * | 10/2005 | Minami et al. | ................ | 131/284 |

(Continued)

FOREIGN PATENT DOCUMENTS

JP    4-95830 A    3/1992

(Continued)

OTHER PUBLICATIONS

International Search Repor for PCT/JP2007/057530, mailing date of Jul. 10, 2007.

*Primary Examiner* — Zarni Maung
(74) *Attorney, Agent, or Firm* — Westerman, Hattori, Daniels & Adrian, LLP

(57) ABSTRACT

Object: To provide an inspecting method and device which can distinguish black dirt, non-black dirt and a tear, without determining a pattern as a defect, in a defect inspection of dirt, a tear, a deformed shape, etc. in sheet-like products having differences in color reproducibility (such as variations, color unevenness and/or color fading).

Solving Means: A sheet-like product inspecting method and device are characterized in preparing an inspection plate having a plurality of different color regions and a color camera capable of picking up images of plural lines of R, G and B components, acquiring R, G and B image data of a sheet-like product that is passed over the inspection plate, obtaining a synthesized image of an R component image, a G component image, and a B component image, detecting a color changed region in the synthesized image, and determining a defect type depending on whether a color of the color changed region falls within a certain range of setting parameter, which is stored in advance per defect type.

14 Claims, 10 Drawing Sheets

U.S. PATENT DOCUMENTS

2007/0052988 A1* 3/2007 Matsuoka et al. ............. 358/1.9
2010/0092190 A1* 4/2010 Numata et al. .................. 399/45

FOREIGN PATENT DOCUMENTS

| JP | 5-205050 A | 8/1993 |
|---|---|---|
| JP | 8-221633 A | 8/1996 |
| JP | 8-276100 A | 10/1996 |
| JP | 9-33348 A | 2/1997 |
| JP | 2000-329701 A | 11/2000 |
| JP | 3685522 B2 | 8/2005 |
| JP | 3813121 B2 | 8/2006 |

* cited by examiner (a)

(b)

SHEET-LIKE PRODUCT INSPECTING METHOD AND DEVICE

TECHNICAL FIELD

The present invention relates to a defect inspecting method and device in continuous processing of a sheet-like product. More particularly, the present invention relates to an inspecting method and device which can distinguish black dirt, non-black dirt and a tear, without determining a pattern to be a defect, in a defect inspection of dirt, a tear, a deformed shape, etc. in sheet-like products having differences in color reproducibility (such as variations, color unevenness, and/or color fading).

BACKGROUND ART

Hitherto, a device for inspecting a defect in one side of a cloth has been proposed which inspects the surface of the cloth that is spread over a belt and is moved together with the belt to be folded after being washed with water, dried and ironed. The proposed device automatically inspects a defect, such as a damage and dirt, in one side of the cloth by illuminating light to the one side of the cloth, capturing the light reflecting from the one side of the cloth by a camera or the like, converting the intensity of light of an image captured by the camera or the like (the intensity of light reflecting from a defective portion is relatively weak) to an electric signal, and processing the converted electric signal. (See Patent Document 1)

Also, there is known a method of, in that type of inspecting device, comparing the converted electric signal with a regular pattern program that is stored in advance, and canceling a pattern signal from the converted electric signal, thus selecting only a signal representing a defect of the cloth (see Patent Document 2).

With the known device, however, because the timings of starting and ending the inspection are adjusted by using sensors to detect the presence of the cloth, problems arise in the following points. An operation failure is caused in the event of malfunction of sensors. Masking for the surroundings is fixed depending on the installed position of each sensor, and only linear masking can be performed at a front end or a rear end.

Further, in a known inspecting device using a line image sensor, detection adjustment is performed by placing a defective sample on a stopped conveyor and confirming a detected level along a line. In practice, however, such detection adjustment may often malfunction because an image of a flowing cloth includes larger noises, which are caused by wrinkles, texture, etc., than those generated in a standstill state. In addition, such detection adjustment requires to be performed for each of defect types in cloths flowing on the conveyor. It is, however, difficult to determine a proper level and to accurately perform the detection for the reasons that even the same type defect as that in the defective sample does not appear constant when the conveyor including cloths passes, and that the conveyor is moved at a high speed.

Therefore, the applicant has previously proposed a cloth inspecting device comprising a conveyor mechanism, a rotation sensor for detecting a conveyance speed of a cloth, an illumination device, an input unit for picking up a line-form image of an inspection target portion of the cloth, a storage unit for storing, as two-dimensional image data, line-form image data from the input unit, a defect information storage unit for storing cloth defect information, a processing unit for determining a defect in the two-dimensional image data, which is stored in the storage unit, based on detection setting information that is input, and when the defect is detected, transmitting defect information to the defect information storage unit, and a folding-up unit including a plurality of cloth folding means disposed in the conveyor mechanism and discharge means for discharging the cloth to a predetermined location depending on the number of times of folding (i.e., the number of parts divided by folding), wherein the processing unit transmits the defect information to the folding-up unit, and the folding-up unit discharges the cloths in different numbers of times of folding based on the defect information from the processing unit (see Patent Document 3).

As one example of a method for inspecting a defective portion, such as a hole or dirt, which is generated in the surface of a sheet-like product made of cloth or paper, for example, there is proposed a method comprising the steps of arranging a plurality of inspection plates having surfaces in different colors side by side, moving the sheet-like product to pass over the surfaces of the inspection plates, and determining color changes which occur in the defective portion of the surface of the sheet-like product when passing over the inspection plates, thereby inspecting a defect in the surface of the sheet-like product (see Patent Document 4).

As one example of a device for inspecting a color difference in a sheet-like product by using a color sensor, there is proposed a device comprising a first CPU for controlling means which conveys the sheet-like product, an input unit for entering inspection conditions, a first display unit for displaying the inspection conditions, and controlling a first output unit for outputting initial conditions, three color sensors, and a second CPU for controlling the color sensors, a second display unit for displaying a detection result, and a second output unit for outputting the detection result, wherein the second CPU processes colorimetric data, which is obtained by the color sensors, to determine a color difference value with respect to a reference color value and a brightness deviation value, displays those values in real time on the second display unit in the form of graphs, and instructs the second output unit to print out the graphs at the end of inspection (see Patent Document 5).

Patent Document 1: Japanese Patent No. 3685522
Patent Document 2: Japanese Patent Laid-Open No. H8-276100
Patent Document 3: Japanese Patent No. 3813121
Patent Document 4: Japanese Patent Laid-Open No. 2000-329701
Patent Document 5: Japanese Patent Laid-Open No. H9-33348

DISCLOSURE OF THE INVENTION

Problems to be Solved by the Invention

In the known device, when a pattern is formed on the sheet-like product made of cloth or paper, for example, the pattern is often determined to be a defect. Particularly, when the state of the sheet-like product placed on the conveyor (the state including the orientation of the sheet-like product and which side thereof is positioned on the face) is not constant like a cloth after being washed, a difficulty arises in masking a particular area of the sheet-like product. On the other hand, it is also practically difficult to place the sheet-like products in the uniform state for the purpose of inspection because the number of work steps is excessively increased.

Patent Document 2 discloses the method of storing the pattern signal in advance. However, the number of comparison targets increases as the number of kinds of cloths increases, and the pattern has to be prepared for each of different orientations of the cloths in consideration of a possibility that the cloths are placed in the different orientations. Thus, the working speed reduces because of the necessity of confirming matching with individual data representing various patterns.

The invention described in Patent Document 4 can determine the presence or absence of a hole in the sheet-like product, but it cannot discriminatively determine the difference between dirt and a pattern.

The problems with an external appearance inspection of sheet-like products having differences in color reproducibility cannot be solved in many cases even by applying the known techniques of general external appearance inspections. The reason is as follows. The general external appearance inspections are based on the technical concept of detecting an abnormality on the premise that products are in a state having a constant level of quality. On the other hand, the external appearance inspection of the sheet-like products having differences in color reproducibility has to be performed on the premise that there are differences in quality, color, etc. of the products. Particularly, in the case of washing and finishing cloths such as sheets, covers, kerchiefs and tablecloths, it is a matter of course that even the same type of products are in different states. More specifically, those products are not uniform in quality and color, and their states are also not uniform when they are placed on, e.g., the conveyor and are carried with it. In addition, the cloths after being washed have a range of quality allowable for delivery to customers. Those products have such a peculiarity that even when the products have wrinkles, slight dirt, etc. on the surfaces, they should not be determined to be defective, and that the determination criteria differs depending on a service level set for each customer.

Accordingly, an object of the present invention is to provide a sheet-like product inspecting method and device, which can solve the above-described problems.

Means for Solving the Problems

To solve the above-described problems, the inventor has first studied a method of masking a particular color. In the sheet-like products having differences (variations) in color reproducibility, such as cloths after being washed, the color of a pattern, e.g., a logo, is not uniform due to discoloring caused by washing. It is, therefore, difficult to mask the particular color.

Here, the term "color" means a property discriminatively perceived by the sense of vision, i.e., by the sense of visual perception depending on differences in a spectral composition of light waves. However, the color is not determined only by the wavelength of light, and it is generally defined by three factors, i.e., a hue (corresponding to the wavelength of monochromatic light), saturation (freshness, i.e., a degree at which the color is less whitey), and luminosity (brightness, i.e., the intensity of light).

As a result of intensive studies, the inventor has gained the finding that the hue of a sheet-like product is kept even after discoloring caused by washing, etc. On the basis of such finding, the inventor has succeeded in masking a pattern by representing the hue of a particular color in terms of numerical value, setting a certain range with the particular numerical value being a reference value, and determining that the color falling within the certain range indicates a pattern.

To increase accuracy in detection, it is preferable to add a step of narrowing data in terms of area. False detection can be minimized by determining the detection target to be a pattern only when a detected colored portion falls within a certain range of area.

Further, the inventor has succeeded in discriminatively determining non-black dirty, black dirty, and a tear by combining information obtained by a color camera regarding the three primary colors of light with colored inspection plates. Be it noted that the color camera is not limited to the line type, and it may be of the area type. Also, the inspection plates to be used are not limited to a combination of a white plate and a black plate.

More specifically, according to a first aspect of the present invention, there is provided a sheet-like product inspecting method comprising the steps of preparing an inspection plate having a plurality of different color regions and a color camera capable of picking up images of plural lines of R, G and B components, acquiring R, G and B image data of a sheet-like product that is passed over the inspection plate, obtaining a synthesized image of an R component image, a G component image, and a B component image, detecting a color changed region in the synthesized image, and determining a defect type depending on whether a color of the color changed region falls within a certain range of setting parameter, which is stored in advance per defect type, wherein the defect type is determined by making the R, G and B lines correspondent to the color regions of the inspection plate in a predetermined relation, and by synthesizing the picked-up R, G and B image data such that the color of the color changed region is emphasized. The color camera may be prepared one or plural.

According to a second aspect of the present invention, there is provided a sheet-like product inspecting method comprising the steps of acquiring R, G and B image data of a sheet-like product put on a conveying mechanism after being washed, detecting a color changed region in the acquired R, G and B image data, executing a masking process when a color of the color changed region falls within a certain range of setting parameter, which is stored in advance per pattern type, and determining the defect type for a product region remaining after the masking process, wherein the setting parameter for determining the pattern type specifies a hue range.

According to a third aspect of the present invention, in the sheet-like product inspecting method according to the second aspect, correspondence information between each pattern type and an area is stored in advance, and the masking process is executed only when the color of the color changed region falls within the certain range of setting parameter, which is stored in advance per pattern type, and when an area of the color changed region satisfies the stored correlation.

According to a fourth aspect of the present invention, in the sheet-like product inspecting method according to the second or third aspect, correspondence information between each pattern type and an aspect ratio is stored in advance, and the masking process is executed only when the color of the color changed region falls within the certain range of setting parameter, which is stored in advance per pattern type, and when an aspect ratio of the color changed region satisfies the stored correlation.

According to a fifth aspect of the present invention, the certain range of setting parameter is set by representing a hue component of a designated color in terms of a numerical value, and by adding and subtracting a predetermined value to and from the numerical value. The color designation is made, for example, by selecting a desired color from a color pallet displayed on a screen, or by clicking an arbitrary portion in a taken-in sample image.

According to a sixth aspect of the present invention, in the sheet-like product inspecting method according to any one of the first to fifth aspects, when the color changed region falling within the previously stored certain range of setting parameter is detected, the sheet-like product is folded in a preset number of times based on previously stored correspondence information between a number of times of folding and a range of the setting parameter, the folded sheet-like product being discharged.

According to a seventh aspect of the present invention, in the sheet-like product inspecting method according to any one of the first to sixth aspects, the sheet-like product is a sheet-like product after being washed.

According to an eighth aspect of the present invention, there is provided a sheet-like product inspecting device comprising a conveying mechanism for conveying a sheet-like product put thereon, an illumination device for illuminating the sheet-like product on the conveying mechanism, an input unit for acquiring R, G and B image data of the sheet-like product on the conveying mechanism, a main storage unit for storing the R, G and B image data from the input unit and defect information of the sheet-like product, a processing unit for detecting a color changed region based on the R, G and B image data stored in the main storage unit, and for determining the presence of a defect, and discharge means for discharging the sheet-like product to a predetermined place, wherein the R, G and B image data of a sheet-like product passing over an inspection plate are acquired, a synthesized image of an R component image, a G component image, and a B component image is obtained, a color changed region is detected in the synthesized image, and a defect type is determined depending on whether a color of the color changed region falls within a certain range of setting parameter, which is stored in the main storage unit per defect type, the processing unit determining the defect type by making the R, G and B lines correspondent to the color regions of the inspection plate in a predetermined relation, and by synthesizing the picked-up R, G and B image data such that the color of the color changed region is emphasized.

According to a ninth aspect of the present invention, there is provided a sheet-like product inspecting device comprising a conveying mechanism for conveying a sheet-like product put thereon after being washed, an inspection plate disposed on the conveying mechanism and having a plurality of different color regions, an illumination device for illuminating the sheet-like product on the conveying mechanism, an input unit for acquiring R, G and B image data of the sheet-like product on the conveying mechanism, a main storage unit for storing the R, G and B image data from the input unit and defect information of the sheet-like product, a processing unit for detecting a color changed region based on the R, G and B image data stored in the main storage unit, and for determining the presence of a defect, a plurality of folding means disposed in the conveying mechanism, and discharge means for discharging the sheet-like product to a predetermined place depending on the number of times of folding, wherein when a color of the color changed region detected by the processing unit falls within a certain range of setting parameter, which is stored in the main storage unit per pattern type, the processing unit executes a masking process on the detected color changed region, the setting parameter for determining the pattern type specifying a hue range.

According to a tenth aspect of the present invention, in the sheet-like product inspecting method according to the ninth aspect, correspondence information between each pattern type and an area is stored in the main storage unit in advance, and the processing unit executes the masking process only when the color changed region falls within the certain range of setting parameter, which is stored in the main storage unit per pattern type, and when an area of the color changed region satisfies the stored correlation.

According to an eleventh aspect of the present invention, in the sheet-like product inspecting method according to the ninth or tenth aspect, correspondence information between each pattern type and an aspect ratio is stored in the main storage unit in advance, and the processing unit executes the masking process only when the color changed region falls within the certain range of setting parameter, which is stored in the main storage unit per pattern type, and when an aspect ratio of the color changed region satisfies the stored correlation.

According to a twelfth aspect of the present invention, in the sheet-like product inspecting method according to any one of the ninth to eleventh aspects, when the color changed region falling within the certain range of setting parameter, which is stored in the main storage unit, is detected, the sheet-like product is folded in a preset number of times based on previously stored correspondence information between a number of times of folding and a range of the setting parameter, the folded sheet-like product being discharged.

According to a thirteenth aspect of the present invention, in the sheet-like product inspecting method according to any one of the eighth to twelfth aspects, the processing unit sets the certain range of setting parameter by representing a hue component of a designated color in terms of a numerical value, and by adding and subtracting a predetermined value to and from the numerical value.

According to a fourteenth aspect of the present invention, in the sheet-like product inspecting method according to any one of the eighth to thirteenth aspects, the sheet-like product is a sheet-like product after being washed.

Effect of the Invention

The present invention enables an inspection to be performed on the sheet-like product causing differences in color reproducibility. Also, even when the sheet-like product has a pattern, the inspection can be performed without determining the pattern to be a defect.

DESCRIPTION OF REFERENCE CHARACTERS

Figure 1:
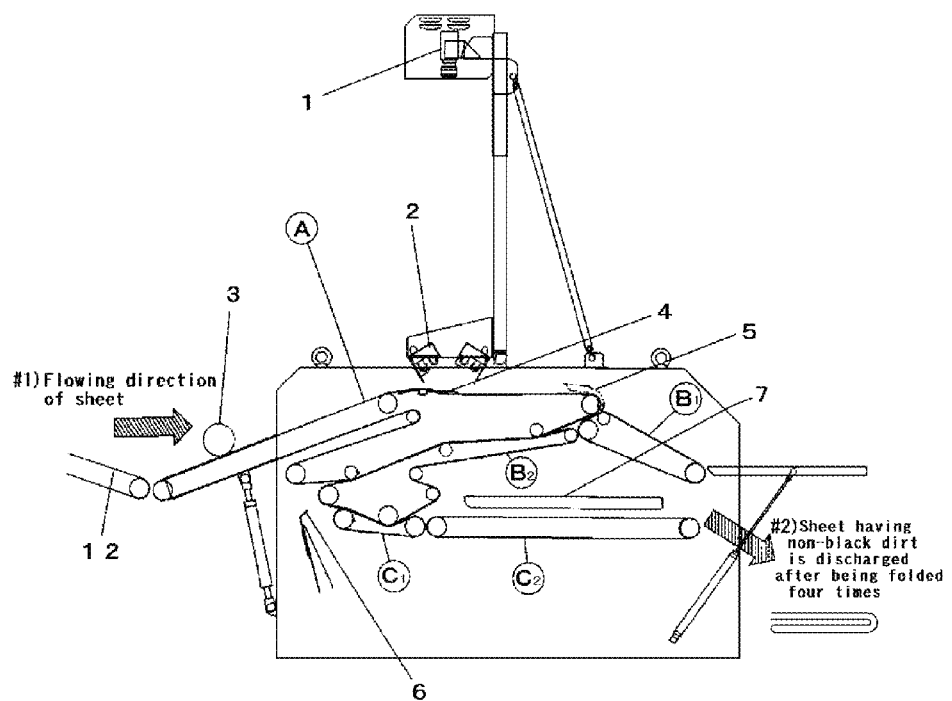
FIG. 1 is a front view of a cloth inspecting device.
Figure 2:
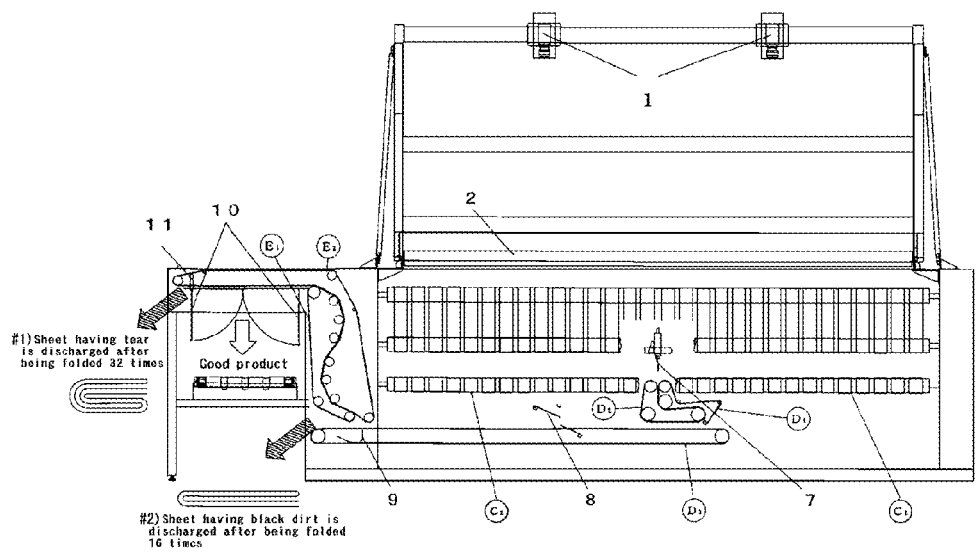
FIG. 2 is a side view of the cloth inspecting device.

1 color camera
2 illumination device
3 rotation sensor
4 inspection stand
5 two-folding means
6 four-folding means
7 eight-folding means
8 16-folding means
9 32-folding means
10 stacker plate
11 discharge hole opening/closing plate
12 roll ironer conveyor
20 input unit
21 processing unit
22 storage unit
23 inspection state storage unit
24 defect information storage unit
25 output unit
26 illumination controller unit
27 display unit
28 rejecter
30 conveyor mechanism
50 cloth
51 non-black dirt
52 tear (hole)
53 black dirt (dirt in black or in color close to black)
60 inspection plate
61 white plate
62 black plate
A1 to E2 folder conveyors

BEST MODE FOR CARRYING OUT THE INVENTION

An inspecting device in the best mode for carrying out the present invention will be described below, by way of example, in connection with a device for inspecting a cloth after being washed. The device for inspecting a cloth after being washed, according to the best mode of the present invention, includes the following components.

1) An image sensor unit (color camera (1)) for taking in a color image along a line and converting the color image to an electric signal 2) A rotation sensor (3) for detecting a moving speed of a work 3) A defect inspection stand (4) used in picking up an image of the work passing over an inspection plate 4) An input unit (20) for receiving a signal from the rotation sensor to send an image pickup start signal to the color camera, receiving the electric signal of the line-form image, which has been picked up by the color camera, for successive conversion to numerical values, and transferring the converted numerical values to the processing unit 5) A processing unit (21) for executing a masking process on image data and transferring defect position information and defect type information (tear, black dirt and non-black dirt), which have been detected from comparison with a defect level, to a defect information storage unit 6) A storage unit (22) for storing two-dimensional RGB images obtained from the line-form image data which has been transferred from the processing unit 7) An inspection state storage unit (23) for discriminatively determining the image data and detecting the presence or absence of the work 8) A defect information storage unit (24) for storing the defect position information and the defect type information, which have been received from the processing unit 9) An output unit (25) for outputting a reject signal based on the defect position information and the defect type information, which are stored in the defect information storage unit 10) An illumination controller unit (26) capable of illuminating an inspection target portion along a line while increasing and decreasing the amount of light 11) A display unit (27) for displaying the information stored in the defect information storage unit and the two-dimensional RGB images 12) A rejecter (28) for rejecting the cloth upon receiving the reject signal 13) An inspection plate (60) having a color region comprised of a black plate and a white plate The color camera used in the present invention is a color camera capable of picking up images of plural lines of R, G and B components. The color camera in the best mode is of, by way of example, the single-plate 3-line type. However, the color camera is not limited to that type, and it may be of the area type. Which type is to be used is decided depending on the size of an inspection target and the working speed.

The defect type can be determined by picking up the images of the plural lines of R, G and B components on the inspection plate which is held in a fixed position, and by synthesizing those images to generate a synthesized image.

In Patent Document 4, because the monochrome line camera is used, it is just possible to determine whether the detected defective portion is a tear. On the other hand, determination of the defect type can be realized with the present invention by using the color camera and the inspection plate in such a combined manner that an achromatic color and a chromatic color are discriminated from each other.

Further, the device for inspecting a cloth after being washed, according to the best mode of the present invention, has the following functions.

(I) Image Data Taking-in Function

This function enables two-dimensional RGB images of the cloth, which is conveyed by a conveying mechanism, to be stored in storage means. Image data is in the form obtained by two-dimensionally taking in an image of in the flowing inspection target and includes noises caused by not only the defective portion, but also by wrinkles, texture, etc. The necessity of repeatedly conveying a sample cloth can be eliminated because an adjustment is performed by utilizing the stored image data instead of an actually input electric signal.

(II) Amount-of-Light Adjusting Function

This function enables an amount of input light to be automatically adjusted constant by increasing and decreasing the amount of light based on the image data that has been taken in from the image sensor. A more stable inspection can be realized because the adjustment is performed by increasing and decreasing the amount of light without amplifying noises in the electric signal.

(III) Basic Masking Function

The presence or absence of a defect is determined based on the taken-in image data. A region as the inspection target is determined by executing a masking process on the image data. Because the masking process is executed on the image data, it is possible to execute a masking process on in a curved form over a certain distance along a hem (edge) of the detected cloth. Further, masking can be performed over a designated width from a center position of the detected cloth.

(IV) Color Masking Function

The color masking function masks a pattern, such as a logo and a design, which is formed on the cloth. The color of the pattern, such as the logo and the design, is changed in a stepless way due to dehydration in a washing process, and hence a difficulty arises in setting a particular color as a reference in advance. Therefore, a color range is prepared by setting, as a reference, a numerical value obtained for a designated color through a predetermined algorithm. Then, a masking process is executed by determining the inspection target to be a pattern if the inspection result falls within the set color range. The determination regarding the presence or absence of a pattern is performed by converting hue, which is changed with certain regularity even when the color is faded, to a numerical value, but it may also be performed by using saturation and brightness in a combined manner. Concrete steps executed by this function are as follows:

i) RGB images are taken in for each cloth.

ii) The color data is taken in while designating a portion to be masked.

iii) The taken-in color is converted to a point within a color space, such as HSV, and hue is converted to a numerical value. In the HSV color space, for example, hue is converted to a degree (e.g., any of 0 to 360 degrees). Therefore, a color is designated by setting thresholds on both sides larger than and smaller than a designated degree (for example, the color range for red is set with 0 degree being at a center).

iv) The color masking process is executed by using the color range which has been calculated based on the setting value.

The pattern, such as the logo and the design, can be precisely masked through the above-described procedures.

(V) Pattern-Related Information Storing Function

The present invention is applied to the business in such a model that used cloths are routinely carried in from particular users. Therefore, false determination in the color masking process can be minimized by storing information related to cloth patterns which have been subjected to the masking process in the past. In this respect, as described above, it is not preferable to store the cloth patterns themselves as in the method disclosed in Patent Document 2. Also, storing the relationship between each pattern and an area is effective in order to obtain a certain working speed without impairing convenience of workers. By storing that relationship, the inspection target can be determined to be a pattern if abnormal values falling within a particular color range and a particular area range are detected. Data narrowing in the determination process can be executed based on not only an area, but also an aspect ratio, a shape, positional information, etc.

(VI) Defect Type Information Emphasizing Function

Figure 8:
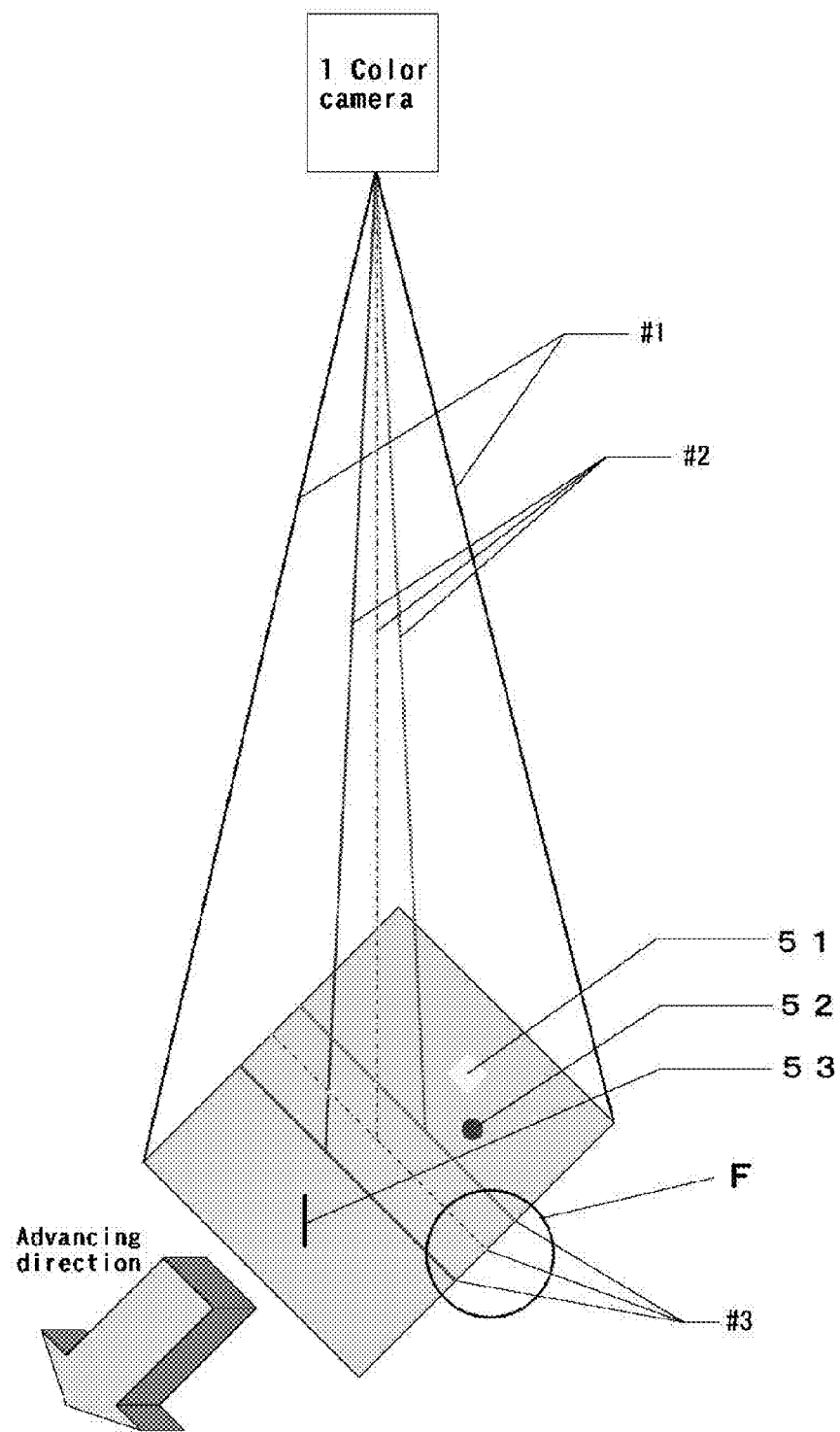
FIG. 8 is an explanatory view to explain a process of taking in R, G and B lines by a color camera.
　#1) area type
　#2) single-plate 3-line type
　#3) three lines are taken-in in the planar direction
Figure 9:
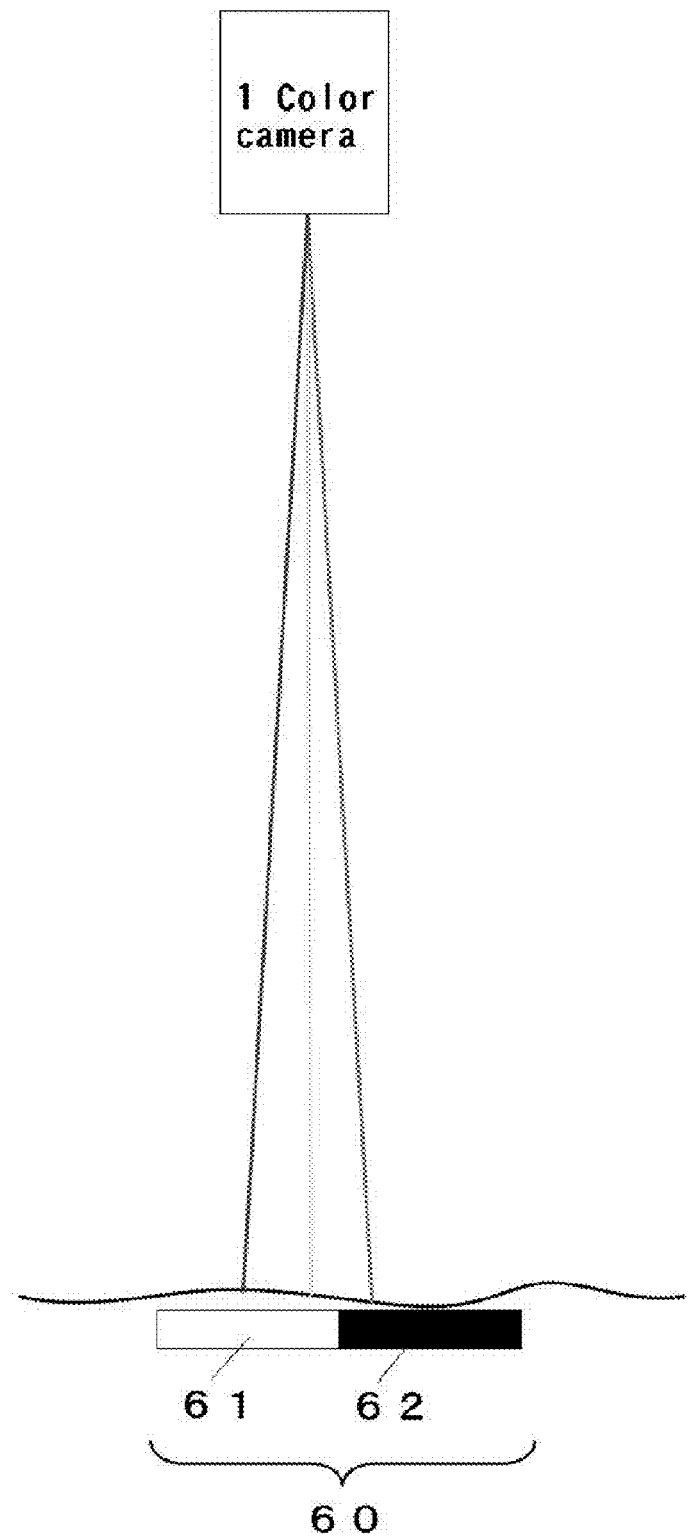
FIG. 9 is an enlarged side view of a region denoted by F in FIG. 8.
Figure 10:
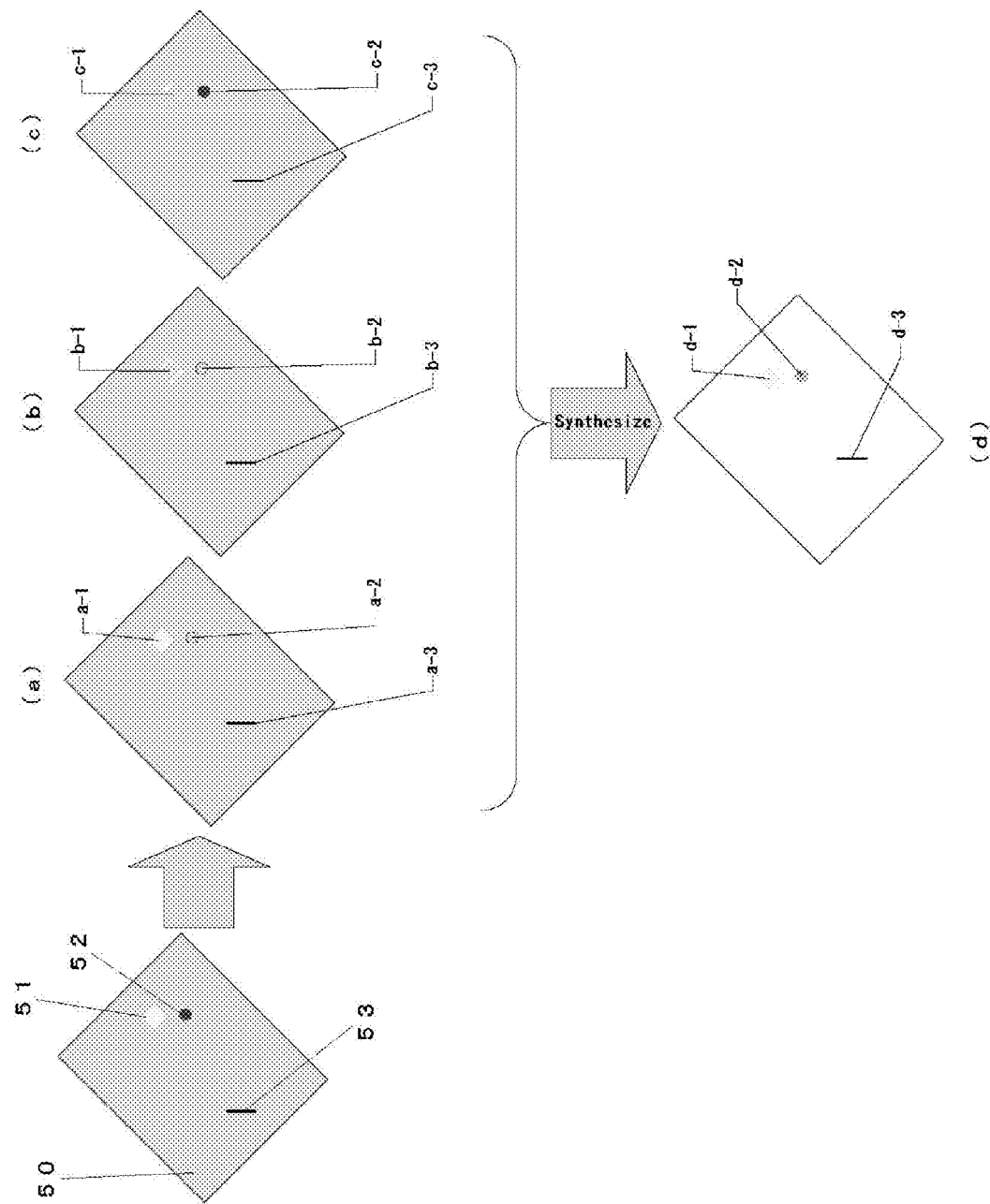
FIG. 10 is an explanatory view to explain a function of emphasizing defect type information.
　(a) blue line (on white plate)
　a-1) becomes deeper
　a-2) disappears
　a-3) becomes darker (b) green line (on white plate)
b-1) shows no change in green color
b-2) disappears
b-3) becomes darker
(c) red line (on black plate)
c-1) shows no change in red color
c-2) becomes very dark
c-3) becomes dark
(d) synthesized image
d-1) non-black dirt (yellow) becomes deeper in yellow color
d-2) a tear become a color close to cyan
d-3) black dirt is taken in as it is

Tear information and dirt information are detected as noises in image data of a work, but it is difficult to precisely determine the defect types from the detected noises. However, the defect type information can be emphasized by conveying the work over the inspection plate having a plurality of color regions, and by utilizing characteristics of the three primary colors of light. More specifically, as illustrated in FIGS. 8 to 10, synthesized image data including the emphasized defect type information can be obtained by arranging three R, G and B lines and the color regions of the inspection plate in a predetermined correspondence relation, and by synthesizing respective picked-up image data of R, G and B together. In FIG. 8, a character (51) denotes non-black dirt in yellowish color, a character (52) denotes a tear, and a character (53) denotes dirt in black or in color close to black. In FIGS. 8 and 9, a left blue line and a central green line are positioned on a white plate (61), while a right red line is positioned on a black plate (62). Even when the color camera (1) is of the area type, the same effect can be obtained by properly setting color components which are extracted respectively at predetermined positions.

When a defective portion including dirt, for example, passes across the color lines, an image of the defective portion is picked up in a state that the color of the defective portion is changed. An image of non-black dirt is changed to become deeper with the presence of the line in a particular color, and an image of a tear is changed to a dark color close to black when passing over the black plate (62). By synthesizing those images, therefore, image data including the emphasized defect type information can be obtained. The color changes occur based on the so-called additive color mixing.

With the above-described processing, the discriminative determination between black dirty and a tear can be easily made which has been difficult to realize in the past. It is needless to say that the combination between the R, G and B lines and the inspection plate (60) is not limited to the above-described example.

(VII) Discharge Function Per Defect Type

The present invention provides the function of discharging cloths in states folded in different numbers of times based on the defect type information (tear, black dirt and non-black dirt). For example, when the inspected cloth has a tear, it is discharged in a state folded in a larger number of times so as to minimize an area occupied by the cloth having a tear. The inspected cloth having non-black dirt is discharged in a state folded in a smaller number of times so as to facilitate re-inspection by a worker. On that occasion, the cloths having defects are preferably discharged in states folded in different numbers of times by setting the correlation between the range of hue and the defect type information in advance. Referring to an example illustrated in FIG. 10, a tear is detected in color close to cyan. Accordingly, when a color close to cyan is detected, the defective portion is determined to be a tear and the relevant cloth is discharged in a state folded in a predetermined number of times. Similarly, cloths having non-black dirt and black dirt (or dirt in color close to black) can be discharged in states folded in different numbers of times from each other.

Embodiment

Details of the present invention will be described below in connection with an embodiment. It is to be noted that the present invention is in no way limited to the following embodiment.

A cloth inspecting device according to the embodiment comprises (A) a cloth defect detecting section and (B) a folding section (folder). Detailed constructions and operations of those sections are as follows.

<<A. Cloth Defect Detecting Section>>

The cloth defect detecting section constituting the device according to the embodiment includes, as illustrated in FIGS.

1 and 2, the color camera (1) which is disposed above a belt to pick up an image of a cloth on the inspection stand and to convert the picked-up image to an electric signal, the illumination device (2) for illuminating an inspection target portion of the cloth that is spread over the belt, the rotation sensor (3) for detecting a moving speed of the inspection target, and the inspection stand (4) disposed between the belt and the cloth to facilitate the inspection of the cloth.

Figure 3:
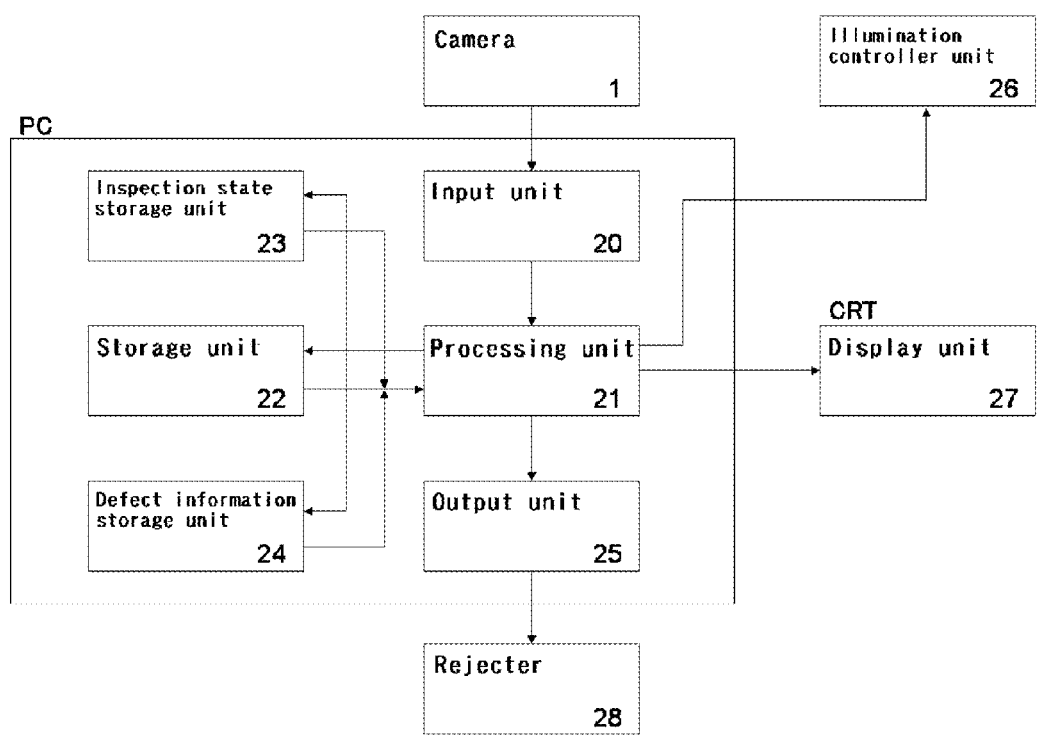
FIG. 3 is a block diagram of a signal processing unit in the cloth inspecting device.

FIG. 3 is a block diagram of a signal processing unit in the cloth inspecting device.

The processing unit (21) issues, based on an input signal from the color camera (1) or information stored in the storage unit, an operation signal to the illumination controller (26) for automatically adjusting an amount of light so as to compensate for a reduction in the amount of light, which is caused by deterioration of a light source and a temperature change, by feeding back a level of the input image. Further, the processing unit (21) executes the masking process on the image data and issues, to the defect information storage unit (24), defect related data corresponding to the type of a defective product, which has been determined in comparison with the setting for defect detection.

The storage unit (22) successively stores line-form signals, thus storing image information in a two-dimensional state. The inspection state storage unit (23) stores information indicating whether the inspection is executed or stopped.

The defect information storage unit (24) stores the defect position information and the defect type information (dirt and tear), which have been detected.

The display unit (27) comprises a display means (CRT) for displaying the taken-in photo information and the determination result.

When the inspection state storage unit (23) indicates that the inspection is executed, the defect determination is made in accordance with the setting for the defect detection. When a defect is detected during the execution of the inspection, the defect position information and the defect type information are stored in the defect information storage unit (24). When the inspection state storage unit (24) indicates that the inspection is stopped, a defect type signal (i.e., a dirt or tear signal) is output based on the information stored in the defect information storage unit (24).

If the defect determination is not ended within a predetermined time, an error is determined or a signal is output based on the information having been input unit at that time. This is because if the defect determination is not ended within the predetermined time, there is a possibility that the relevant cloth reaches the folding process before the end of the defect determination. A time during which the defect determination is to be ended can be set as a matter of design that is determined depending on the size of the cloth, i.e., the inspection target, and the correlation between the defect type information and the number of times of folding (i.e., the number of parts divided by folding).

<<B. Folding Section (Folder)>>

The folding section includes a conveyor mechanism (30) comprising a plurality of conveyors A1 to E2 which convey the cloth carried from an ironer to a stacker, a plurality of cloth folding means (5) to (9) disposed inside the conveyor mechanism (30), and a stacker device for discharging defective products and stocking good products.

The conveyor mechanism (30) comprises a conveyor A (folder conveyor) for receiving the cloth from a roll ironer conveyor (12) and taking the pressed cloth into the folder, a conveyor B1 disposed so as to extend forwardly of the conveyor A and being able to run in a switchable way between the same direction as the conveyor A and the opposed direction, a conveyor B2 disposed under the conveyor A and conveying the cloth, which has been carried over from the conveyor B1 in a two-folded state when the running direction of the conveyor B1 is switched over, while grasping the two-folded cloth between the conveyor B2 and the underside of the conveyor A, a conveyor C1 disposed under the conveyor B2 and conveying the cloth, which has been pushed onto the conveyor C1 by a four-folding means (6), while grasping the four-folded cloth between the conveyor C1 and the underside of the conveyor B2, a pair of conveyors C2 and C2 disposed so as to extend from the conveyor C1, arranged parallel to each other in the conveying direction with a predetermined gap left therebetween, and being switchable between run and stop, conveyors D1 and D2 disposed under the conveyors C2 perpendicularly to the conveyors C2, having receiving portions positioned in the gap between the pair of conveyors C2 and C2, and conveying the cloth, which has been pushed onto the conveyors D1 and D2 by an eight-folding means (7), while grasping the eight-folded cloth between the conveyors D1 and D2, a conveyor D3 disposed under the conveyors D1 and D2 so as to define the conveying direction changed through 90 degrees, and including a 16-folded means (8) in its intermediate portion, and conveyors E1 and E2 disposed above the conveyor D3 and conveying the cloth, which has been pushed onto the conveyors E1 and E2 in a 32-folded state, to the stacker device while grasping the 32-folded cloth between the conveyors E1 and E2.

The cloth folding means comprises the two-folding means (5) for folding the cloth into two parts by reversing the running direction of the conveyor B1 in accordance with a folding signal when an intermediate portion of the cloth carried over from the roll ironer conveyor (12) reaches the boundary between the conveyor A and the conveyor B1, and by withdrawing the intermediate portion of the cloth into a gap between the conveyor A and the conveyor B1, the four-folding means (6) disposed opposite to overlapped ends of the conveyor A and the conveyor B2 and folding the two-folded cloth into a four-folded state by pushing an intermediate portion of the two-folded cloth, which has been conveyed in a state grasped between the conveyor A and the conveyor B2, into a gap between the conveyor B2 and the conveyor C1, the eight-folding means (7) disposed above the gap between the pair of conveyors C2 and C2 and folding the four-folded cloth into an eight-folded state by starting to operate at the same time as when the running of the conveyors C2 and C2 is stopped, and by pushing the four-folded cloth into a gap between the pair of conveyors D1 and D2, the 16-folding means (8) arranged in an intermediate portion of the conveyor D3, holding a leading end of the eight-folded cloth while waiting for passage of a tailing end thereof, and releasing the leading end at the same time as when the tailing end passes the 16-folding means (8), and the 32-folding means (9) disposed at a backward end of the conveyor D3 and folding the 16-folded cloth into a 32-folded state by allowing a leading end of the carried 16-folded cloth to pass there, and by pushing an intermediate portion of the 16-folded cloth into a gap between the conveyor E1 and the conveyor E2.

The stacker device is disposed at a backward end of the conveyor E2 and comprises a stacker having a pair of plates which are opened to drop the 32-folded cloth (good product) for stacking, and a discharge port opening/closing plate (11) disposed at a backward end of the conveyor E2 and making the stacker plates inoperative such that the 32-folded cloth can be discharged to the outside of the folder.

<<Defect Inspection>>

Figure 4:
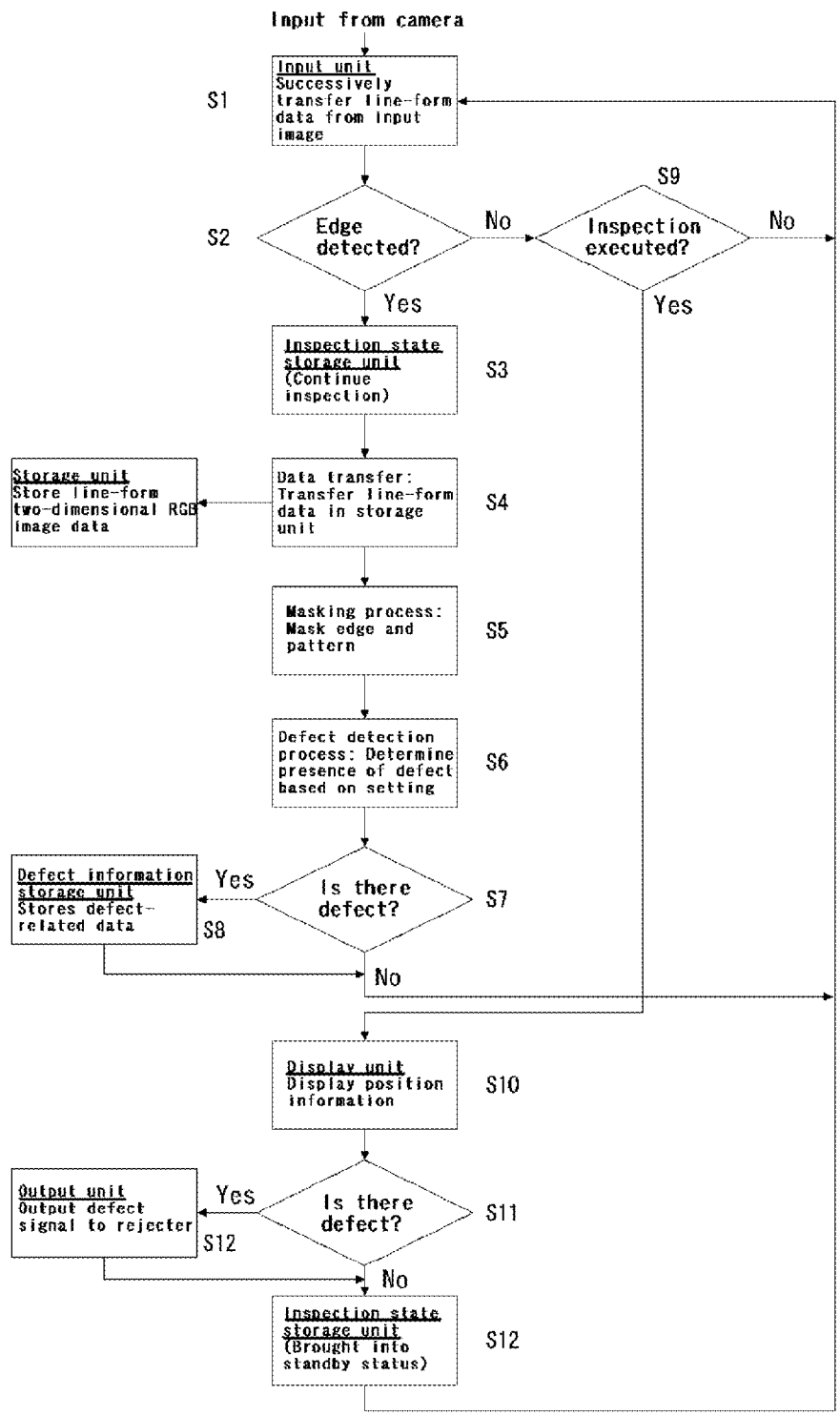
FIG. 4 is a flowchart when the signal processing unit is in an inspection state.

The processing of the cloth defect detecting section when a defect of the cloth is inspected will be described below with reference to FIG. 4.

In accordance with information from the color camera, line-form data is successively transferred from an input image (S1). It is determined whether an edge of the conveyed cloth is detected (S2). If the edge is detected, the inspection is continued (S3). If the edge is not detected, the processing advances to step S9.

If the edge is detected, the inspection is continued (S3) and the line-form data is transferred to the storage unit (S4) to be stored as line-form two-dimensional RGB image data in the storage unit. The basic masking process and the color masking process are executed on the image data stored in the storage unit (S5).

Whether there is a defect is determined based on the setting for the defect detection (S6). If there is a defect, defect-related data is stored in the defect information storage unit (S8). Thereafter, the processing returns to step S1. If there is no defect (S7), the processing also returns to step S1.

If the edge is not detected in step S2, it is determined whether the inspection is executed (S9). If the inspection is executed, position information is displayed on the display unit (S10). If the inspection is not executed, the processing returns to step S1. It is then determined whether there is a defect (S11). If there is a defect, a defect signal is output to the rejecter (28) (S12). If there is no defect, the inspection state storage unit is immediately brought into a standby status (S13) and the processing returns to step S1. Subsequently, the above-described processing is repeated.

The masking processes will be described below additionally.

In the device of this embodiment, two masking processes, i.e., the basic masking process and the color masking process, are executed.

(I) Basic Masking Process

The basic masking process is a masking process to exclude a part of the cloth positioned over a certain distance from the edge (hem) from the inspection target. The reason is that, in the case of the cloth being a sheet or the like, there is no problem in a quality level even if dirt, etc. are present in an edge portion.

In the device of this embodiment, the edge portion can be masked in units of 1 cm at each of the upper, lower, left and right edges. When the cloth is obliquely placed, the masking process is also obliquely executed along an edge line.

Further, a detection level can be adjusted by setting a parameter, which is used in determining a defect, such that the defect is detected only when the parameter is equal to or larger than a predetermined value. The reason is that dirt in an area of not larger than a certain size or at a depth of not higher than a certain level is not problematic in some cases depending on quality criteria set for customers.

(II) Color Masking Process

Figure 7:
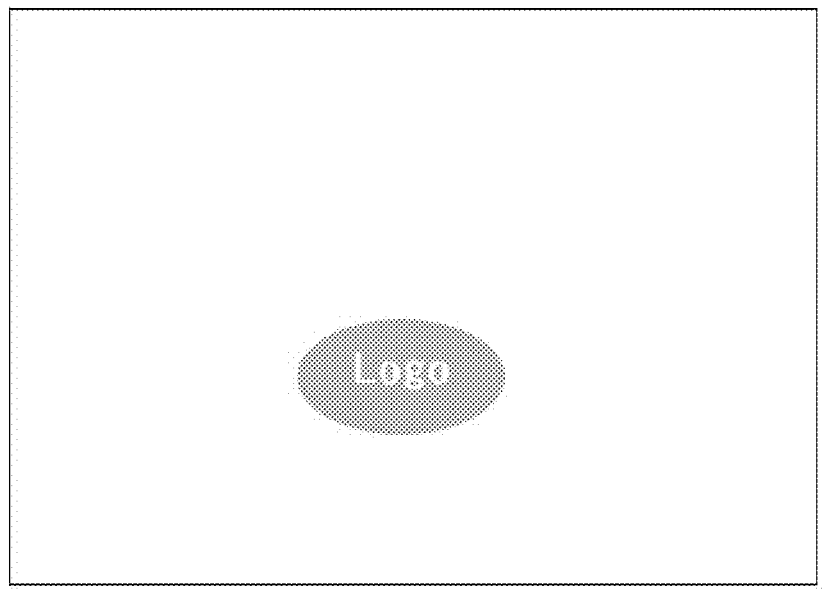
FIG. 7A and FIG. 7B are explanatory views to explain a color masking function.
Figure 7:
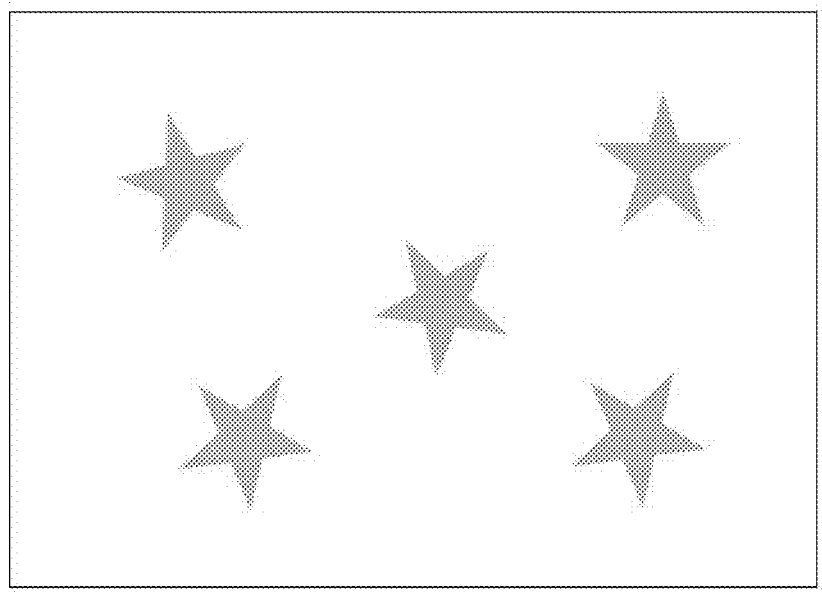

The color masking process is a masking process to prevent a pattern, such as a logo and a design, from being determined to be a defect. For example, when a logo is present on a cloth as illustrated in FIG. 7(a), the logo is determined to be dirt by the known device. To avoid such a problem, the masking process is executed so as to determine a color changed region, which falls within a certain distance range with respect to a designated color (color of the logo), to be not dirt, but a pattern.

In the device of this embodiment, the certain distance range with respect to the designated color is calculated by representing the designated color in terms of HSV color space. In the HSV color space, hue is expressed in terms of degree (e.g., in the range of 0 to 360 degrees). Therefore, a hue range is designated by setting certain thresholds on both sides of the designated degree (e.g., about 0 degree in the case of reddish color).

The designated color is preferably designated to a color after the cloth has been washed several times, instead of designating the color of the pattern on a fresh cloth. With the designated color being set as a reference value, the color changed region falling within a certain hue range (i.e., a certain range of shade) is determined to be a pattern and is excluded by the color masking process. Thus, since colors falling within the certain hue range can be masked, there is no need of manually setting each of all color changed regions to be excluded from the inspection target even in the cloth including the pattern illustrated in FIG. 7(b).

As an additional function for assisting the setting operation, the defect inspecting device may further include the function of, when an arbitrary part of the image data displayed on the display unit is designated, displaying a numerical value that represents the color of the designated part. Also, the defect inspecting device may include the function of displaying, on the display unit, colors which represent an upper limit value and a lower limit value of the certain hue range and which are obtained through reverse transform based on the calculation formula for the HSV color space.

(III) Data Narrowing Based on Stored Information Such as Area

Because the color of a pattern, such as a logo and a design, is not present in the natural world in many cases and dirt having the same color as that of the pattern is hardly attached, the color masking process is expected to be fairly effective in preventing the pattern from being determined to be a defect. From the viewpoint of reducing a possibility of false detection, however, it is more effective to execute narrowing of data based on stored information, such as an area, for example. More specifically, when the color changed region to be excluded by the color masking process does not fall within a predetermined area range, it is exceptionally determined to be not a pattern and is not excluded by the color masking process. The area used in determining whether the color changed region may be set in relation to hue, or it may be set such that the color changed region is not determined to be a defect unconditionally when the area is not smaller than or not larger than a certain value.

(IV) Defect Type Information Emphasizing Process

The pattern determination can be made with higher reliability by executing a defect type information emphasizing process prior to the pattern determination process. To describe in more detail in connection with concrete examples, the yellowish non-black dirt (51) is changed to become deeper in blue-line image data (FIG. 10a) and can be captured as deeper yellowish dirt when the blue-line image data is synthesized with green-line image data (FIG. 10b) and red-line image data (FIG. 10c). Further, the tear (52) can be captured as a black image only on the black plate (61) (corresponding to the red line) and hence can be captured as an image in color close to cyan in the synthesized image data. The black dirt (53) appears with no change even after synthesizing the image data for the three lines. Thus, a pattern falling within the certain hue range with respect to cyan can be determined to be a tear with a high probability.

<<Setting>>

In order to operate the inspecting device so as to detect a defect sample as an inspection target, it is required to perform sensitivity setting in the inspecting device depending on the defect. The sensitivity setting is performed as follows.

1) The defect sample is moved with the conveyor to pass the inspecting device, and two-dimensional RGB image data is stored.

2) The basic masking process and the color masking process are executed on the stored image data.

3) By using the image data after being subjected to the masking processes, the inspection is performed based on the setting for the detection, which is optionally selected.

4) A photo image and the image data after being subjected to the masking processes are comparatively displayed on the display unit. At that time, the detected defect position is colored.

5) The setting for the detection is changed such that the defect position displayed based on the image data matches with a corresponding defect position on the photo image. Thereafter, the above-described steps 2) to 5) are repeated again.

6) The setting for the detection for the relevant defect sample is finally defined upon confirming that the defect position based on the image data matches with the corresponding defect position on the photo image.

Figure 5:
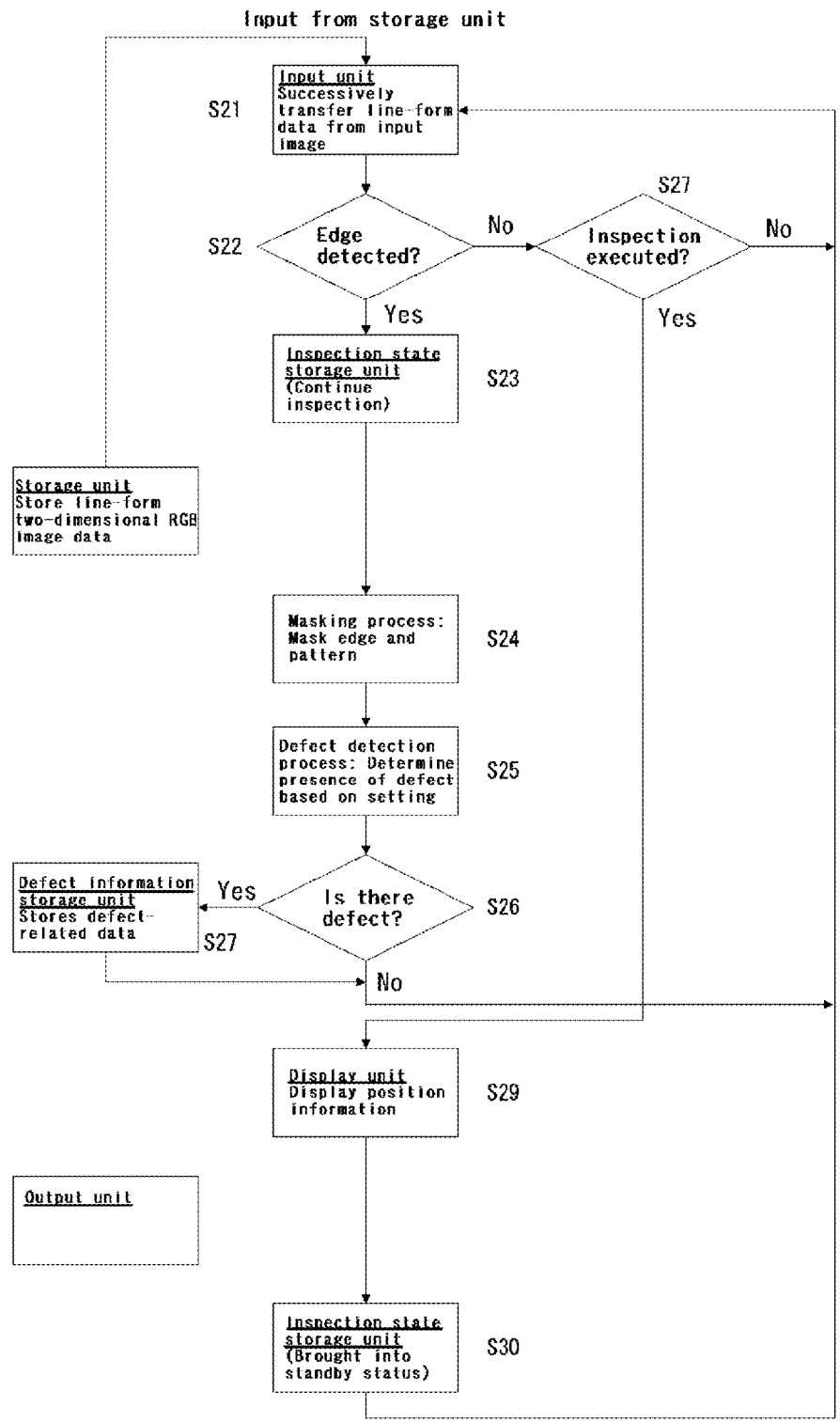
FIG. 5 is a flowchart when the signal processing unit is in an adjustment state.

The defect detection in the setting operation is executed as per illustrated in FIG. 5. Procedures in FIG. 5 are substantially the same as those in FIG. 4 except that the image stored in the storage unit is used instead of an image input from the camera.

<<Discharging Process>>

When there is a defect in a cloth after being washed, the cloth is discharged after being folded in different numbers of times depending on the defect types. The cloth having dirt and the cloth having a tear are discharged to the outside of the folder in a four-folded state and a 16-folded state, respectively, without being conveyed to a subsequent step. The normal cloth having no defects is stocked in the stocker in a 32-folded state. Since the cloth having a tear is discarded, it is preferably discharged in a state folded in a larger number of times than the cloth having dirt.

Figure 6:
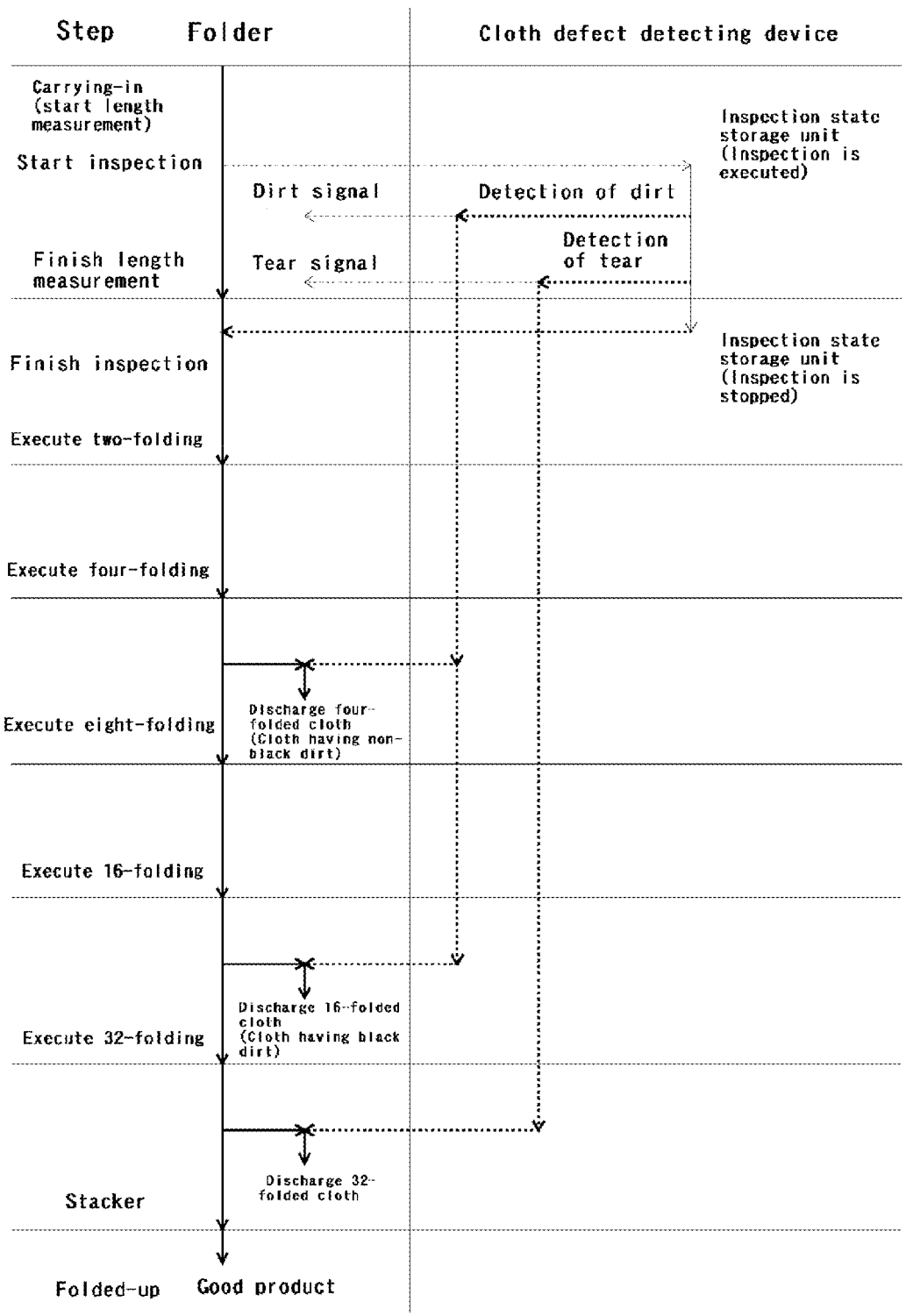
FIG. 6 is a chart to explain successive operation steps.

The operation of the discharging process in the cloth defect inspecting device, which is constructed as described above, will be described below with reference to FIG. 6.

i) When a cloth is carried into the folder, the inspection state storage unit discriminatively determines the input image data and indicates the presence of a work.

ii) An inspection is started when the inspection state storage unit comes into the status indicating the presence of the work, and the inspection is ended when the inspection state storage unit comes into the status indicating the absence of the work. A defect type signal (i.e., a dirt signal or a tear signal) is then output based on the information in the defect information storage unit.

iii) When dirt is detected, an inoperative signal is issued to the cloth eight-folding means. When a tear is detected, an inoperative signal is issued to the cloth 32-folding means and the stacker.

The folder thus constructed operates, as described below, not only to fold the cloths conveyed from an ironer, but also to classify the cloths into good products and defective products in accordance with a signal from the signal processing unit. Further, the folder classifies the defective products into a product having black dirt, a product having non-black dirt and a product having a tear, and then discharges those defective products to predetermined respective discharge outlets.

(1) <Determination Step>

The length and the moving speed of the cloth are measured based on a signal from the rotation sensor and the input image data. Further, the masking processes are executed on the input image data, and the defect type information is determined.

(2) <Two-Folding Step>

The cloth two-folding means is actuated to perform the pushing operation at the timing of two-folding the cloth depending on the measured length and moving speed of the cloth. At the same time, the conveyor B1 is reversed in its running direction such that the cloth is carried into the gap between the conveyor A and the conveyor B1 to be two-folded. The two-folded cloth is supplied to the four-folding means (6) while it is gripped between the conveyor A and the conveyor B2.

(3) <Four-Folding Step>

In a state where the two-folded cloth is supplied from the backward ends of the conveyor A and the conveyor B2 and is hanged between the cloth four-folding means (6) and the conveyor C1, the cloth four-folding means (6) is actuated to push the two-folded cloth into the gap between the conveyor B2 and the conveyor C1 at the timing of further two-folding the cloth such that the two-folded cloth is brought into a four-folded state for supply to the conveyors C1 and C2. The four-folded cloth is supplied to the eight-folding means (7) by the conveyors C1 and C2.

(4) <Eight-Folding Step>

Among the cloths supplied from the four-folding device, good products are each further folded from the four-folded state into an eight-folded state by actuating the eight-folding means (7) so as to push the four-folded cloth into the gap between the conveyor D1 and the conveyor D2. The eight-folded cloth is supplied to the conveyor D3. For products each having non-black dirt, this eight-folding step is controlled to be not performed in accordance with a signal from the signal processing unit. Thus, the product having non-black dirt is discharged in the four-folded state to the outside of the folder. The eight-folded cloth, i.e., the good product, is supplied to the 16-folding means (8) disposed in the intermediate portion of the conveyor D3.

(5) <16-Folding Step>

The eight-folded cloth is further folded into a 16-folded state by moving a 16-folding plate upwards, which is operable in the vertical direction, to hold a leading end of the cloth between the folding plate and a retainer plate positioned above the former, waiting for passage of a tailing end of the cloth, and releasing the leading end at the same time as when the tailing end passes. The 16-folded cloth is supplied to the 32-folding device disposed at the backward end of the conveyor D3.

(6) <32-Folding Step>

Among the cloths supplied from the 16-folding means (8), good products or products having tears are each further folded from the 16-folded state into a 32-folded state by actuating the cloth 32-folding means (9) so as to push the 16-folded cloth into the gap between the conveyor E1 and the conveyor E2. For products each having black dirt, this 32-folding step is controlled to be not performed in accordance with a signal from the signal processing unit. Thus, the product having black dirt is discharged in the 16-folded state to the outside of the folder. The 32-folded cloth is supplied to the stacker while it is gripped between the conveyor E1 and the conveyor E2.

(7) <Stocking Step>

The 32-folded cloth (good product) is dropped to be put one above another in the stocker by opening a pair of stacker plates (10). The product having a tear is discharged in the 32-folded state to the outside of the folder by opening a discharge-outlet opening/closing plate (11) and making the stacker plates (10) inoperative in accordance with respective signals from the signal processing unit.

While, in the embodiment, the cloth is pushed into the gap between the conveyor A and the conveyor B1 by reversing the running direction of the conveyor B1 in the two-folding step, the cloth may be discharged to the outside of the folder without reversing the running direction of the conveyor B1. For example, when the defect type information cannot be detected and an error is caused, the relevant cloth may be immediately discharged to the outside for a supplemental manual check.

Also, while the embodiment is constructed so as to discharge the defective product midway the conveyor mechanism in the folder, a discharging device (like the rejecter (28)) may be disposed midway a conveyor for moving the cloth from the ironer to the folder such that the defective product can be discharged as required.

The invention claimed is:

1. A sheet-like product inspecting method, comprising:
   providing an inspection plate having a light color region and a dark color region and a color camera capable of picking up images of three lines of R, G and B;
   acquiring respective R, G and B image data of the R, G and B lines for a sheet-like product after being washed, which is passed over the inspection plate;
   synthesizing respective images of the R, G and B lines to obtain a synthesized image of the sheet-like product in which a color of a defective portion is emphasized;
   detecting a color changed region in the synthesized image; and
   determining a defect type depending on whether a color of the color changed region falls within a certain range of setting parameter, which is stored in advance for each of defect types including dirt and a tear;
   wherein the images of two among the R, G and B lines are picked up at positions in one of the color regions, and the image of the other one line is picked up at a position in the other color region.

2. The sheet-like product inspecting method according to claim 1, wherein a hue component of a designated color, which is designated in accordance with a pattern on the sheet-like product, is represented in terms of a numerical value, a certain range of setting parameter per pattern type is set based on the numerical value, a masking process is executed when the color changed region falls within the certain range of setting parameter per pattern type, and the presence of a defect is determined for a product region remaining after the masking process.

3. The sheet-like product inspecting method according to claim 2, wherein correspondence information between each pattern type and an area is stored in advance, and the masking process is executed only when the color of the color changed region falls within the certain range of setting parameter, which is stored in advance per pattern type, and when an area of the color changed region satisfies the stored correlation.

4. The sheet-like product inspecting method according to claim 2, wherein correspondence information between each pattern type and an aspect ratio is stored in advance, and the masking process is executed only when the color of the color changed region falls within the certain range of setting parameter, which is stored in advance per pattern type, and when an aspect ratio of the color changed region satisfies the stored correlation.

5. The sheet-like product inspecting method according to claim 1, wherein defect types including a tear, black dirt, and non-black dirt are discriminatively determined.

6. The sheet-like product inspecting method according to claim 1, wherein the sheet-like product is a cloth causing differences in color reproducibility.

7. The sheet-like product inspecting method according to claim 1, wherein the light color region is a white or whitey region and the dark color region is a black or blackish region.

8. A sheet-like product inspecting device comprising a conveying mechanism for conveying a sheet-like product put thereon after being washed, an inspection plate disposed on the conveying mechanism and having a light color region and a dark color region, an illumination device for illuminating the sheet-like product on the conveying mechanism, a color camera capable of picking up images of three lines of R, G and B for the sheet-like product on the conveying mechanism, a main storage unit for storing respective R, G and B image data of the R, G and B lines and defect information of the sheet-like product, and a processing unit for determining the presence of any of defect types including dirt and a tear, the images of two among the R, G and B lines being picked up at positions in one of the color regions, the image of the other one line being picked up at a position in the other color region,
   wherein the processing unit acquires respective R, G and B image data of the R, G and B lines for the sheet-like product after being washed, which is passed over the inspection plate, synthesizes the respective image data of the R, G and B lines to obtain a synthesized image of the sheet-like product in which a color of a defective portion is emphasized, detects a color changed region in the synthesized image, and determines a defect type depending on whether a color of the color changed region falls within a certain range of setting parameter, which is stored in the main storage unit per defect type.

9. The sheet-like product inspecting device according to claim 8, wherein correspondence information between each pattern type and an area is stored in the main storage unit in advance, and
   the processing unit represents a hue component of a designated color, which is designated in accordance with a pattern on the sheet-like product, in terms of a numerical value, sets a certain range of setting parameter per pattern type based on the numerical value, and executes a masking process only when the color changed region falls within the certain range of setting parameter, which is stored in the main storage unit per pattern type, and when an area of the color changed region satisfies the stored correlation.

10. The sheet-like product inspecting device according to claim 8, wherein correspondence information between each pattern type and an aspect ratio is stored in the main storage unit in advance, and
    the processing unit executes the masking process only when the color changed region falls within the certain range of setting parameter, which is stored in the main storage unit per pattern type, and when an aspect ratio of the color changed region satisfies the stored correlation.

11. The sheet-like product inspecting device according to claim 8, further comprising a plurality of folding means disposed in the conveying mechanism and discharge means for discharging the sheet-like product to a predetermined place depending on the number of times of folding,
    wherein when the color changed region falling within the certain range of setting parameter, which is stored in the main storage unit, is detected, the sheet-like product is folded in a preset number of times based on previously stored correspondence information between a number of times of folding and a range of the setting parameter, the folded sheet-like product being discharged.

12. The sheet-like product inspecting device according to claim 8, wherein the defect types including a tear, black dirt, and non-black dirt are discriminatively determined.

13. The sheet-like product inspecting device according to claim 8, wherein the sheet-like product is a cloth causing differences in color reproducibility.

14. The sheet-like product inspecting device according to claim 8, wherein the light color region is a white or whitey region and the dark color region is a black or blackish region.

* * * * *